United States Patent
Tanabe

(10) Patent No.: US 8,048,335 B2
(45) Date of Patent: Nov. 1, 2011

(54) CHOLESTERIC LIQUID CRYSTAL COMPOSITION

(75) Inventor: Mayumi Tanabe, Chiba (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 174 days.

(21) Appl. No.: 12/572,530

(22) Filed: Oct. 2, 2009

(65) Prior Publication Data

US 2010/0086506 A1    Apr. 8, 2010

(30) Foreign Application Priority Data

Oct. 6, 2008   (JP) ................. 2008-259173

(51) Int. Cl.
*C09K 19/36* (2006.01)
*A61K 8/36* (2006.01)

(52) U.S. Cl. ............. 252/299.7; 252/299.01; 424/1.11; 424/401

(58) Field of Classification Search ............. 252/299.01, 252/299.7; 424/401, 1.11

See application file for complete search history.

(56) References Cited

U.S. PATENT DOCUMENTS 6,828,451 B2 * 12/2004 Barrault et al. ................. 554/1
2003/0195367 A1   10/2003 Barrault et al.

FOREIGN PATENT DOCUMENTS

| DE | 252884 | 12/1987 |
| JP | S57-062212 | 4/1982 |
| JP | H03-099094 | 4/1991 |
| JP | H05-310526 | 11/1993 |
| JP | 2001-311079 | 11/2001 |
| JP | 2006-176422 | 7/2006 |

* cited by examiner

*Primary Examiner* — Shean Wu
(74) *Attorney, Agent, or Firm* — J.C. Patents

(57) ABSTRACT

A cholesteric liquid crystal composition containing at least one esterified product selected from the group consisting of (1) an esterified product of a hydrolysate of (A) a γ-oryzanol and (B1) a carboxylic acid compound, (2) an esterified product of a hydrogenated product of a hydrolysate of (A) a γ-oryzanol and (B2) a carboxylic acid compound, and (3) an esterified product of a hydrogenated product of (A) a γ-oryzanol and (B3) a carboxylic acid compound. The γ-oryzanol (A) is a mixture containing at least one ferulate ester of a vegetable sterol and at least one ferulate ester of a triterpene alcohol, and the hydrolysate of the γ-oryzanol (A) is a mixture containing at least one vegetable sterol and at least one triterpene alcohol.

21 Claims, No Drawings

CHOLESTERIC LIQUID CRYSTAL COMPOSITION

CROSS-REFERENCE TO RELATED APPLICATION

This application claims the priority benefit of Japan application serial no. 2008-259173, filed Oct. 6, 2008. The entirety of the above-mentioned patent application is hereby incorporated by reference herein and made a part of specification.

BACKGROUND OF THE INVENTION

1. Field of the Invention

The present invention relates to a cholesteric liquid crystal composition that reflects light having a particular wavelength range around room temperature and body temperature, and a use thereof.

2. Related Art

A cholesteric liquid crystal molecule has a helical structure in a liquid crystal state. Accordingly, upon irradiating a cholesteric liquid crystal phase with light, the liquid crystal phase reflects circularly polarized light having a specific wavelength range corresponding to the rotation direction and the pitch length of the helical structure of the liquid crystal molecule. For example, upon irradiating with visible light, the liquid crystal phase selectively reflects light having a wavelength of blue, green, yellow and red corresponding to the pitch length of the liquid crystal. The color of the reflected light has viewing angle dependency, i.e., changes depending on the viewing angle, which is different from a pigment or dye, which exhibits color by absorption of light. The cholesteric liquid crystal can be controlled in pitch length by the temperature and the species of the compound, and thus can selectively reflect light not only in the visible range but also in a near infrared range or an ultraviolet range.

Materials that selectively reflect light of various wavelengths within a wide wavelength range have been provided by utilizing the characteristics of the cholesteric liquid crystal. Examples of the materials include a liquid crystal pigment, a paint, a spray ink, a printing ink, cosmetics, an anti-counterfeit printed matter and an ornament. Such materials have been proposed as an optical film, such as a polarizing plate, a compensation plate and a color filter, for an optical device, such as a liquid crystal display device and a holography device. The cholesteric liquid crystal pigment, which has been known in the art, includes a cholesteric liquid crystal polymer in a flake form and a microencapsulated cholesteric liquid crystal. JP-A-2001-311079 discloses manufacturing method of a microencapsulated cholesteric liquid crystal. Examples of the purpose thereof include a paint for an automobile and cosmetics.

An animal-derived material (cholesterol) extracted mainly from wool wax has been used as a raw material for the cholesteric liquid crystal (cholesteric material), and in recent years, a vegetable-derived material is receiving attention in view of care for the environment and the human body. The vegetable-derived material is a component extracted from vegetable seeds or various parts of vegetables, and can be obtained, for example, from rice bran, rice bran oil, soybean, wheat, corn, palm, cotton seeds, coleseed or the like. Examples of a vegetable-derived material that exhibits liquid crystallinity include vegetable cholesterol, which is contained in soybean in a large proportion, and a triterpene alcohol derivative, which is obtained from rice bran oil.

DD 252,884 discloses that a sitosterol derivative has a cholesteric phase in a region of 150° C. or more, and a composition thereof has a cholesteric phase around room temperature. The major component of the composition is a cholesterol derivative, to which the characteristics of the cholesterol derivative, i.e., exhibition of a cholesteric phase around room temperature, is reflected.

JP-A-3-99094 discloses that esterified products of triterpene alcohols have a cholesteric phase, but all the esterified products disclosed have a narrow region where a cholesteric phase is exhibited, and no compound is disclosed that has a cholesteric phase within a wide range around room temperature. The triterpene alcohols used therein are contained as mixtures in naturally-derived materials, and it is difficult to isolate them by extraction for industrial use.

JP-T-2004-504291 (the term "JP-T" as used herein means a published Japanese translation of a PCT patent application) discloses, as a vegetable unsaponifiable material, an ester of sterol, stanol or triterpene alcohol with a long-chain fatty acid. The compound is used in such purposes as cosmetics and pharmaceuticals, but JP-T-2004-504291 does not disclose or suggest liquid crystallinity.

JP-A-2006-176422 discloses that an ester of vegetable sterol or triterpene alcohol with a long-chain fatty acid, as a sterol ester obtained from rice bran, is used in such purposes as cosmetics and pharmaceuticals, but JP-A-2006-176422 does not disclose or suggest liquid crystallinity.

JP-A-5-310526 discloses γ-oryzanol, which is an ester of sterol or triterpene alcohol with ferulic acid, and JP-A-57-62212 discloses an esterified product of triterpene alcohol with hydroxybenzoic acid. However, these documents do not disclose or suggest liquid crystallinity.

In the case where a cholesteric material obtained from a vegetable-derived material is used in the cosmetic field, and particularly applied to the human lips and skin, such a material is demanded that exhibits cholesteric reflected color in a temperature range around room temperature or body temperature. Red to purple, preferably red to yellow colors are required to be developed in a temperature range in the vicinity of 0 to 60° C., particularly preferably 20 to 40° C. Accordingly, a cholesteric liquid crystal material is demanded to be controlled in color range with respect to temperature when the material is applied to the cosmetic field for exhibiting esthetic effect thereby.

SUMMARY OF THE INVENTION

The invention relates to a cholesteric liquid crystal composition containing at least one esterified product selected from the group containing:

(1) an esterified product of a hydrolysate of (A) a γ-oryzanol and (B1) a carboxylic acid compound, (2) an esterified product of a hydrogenated product of a hydrolysate of (A) a γ-oryzanol and (B2) a carboxylic acid compound, and (3) an esterified product of a hydrogenated product of (A) a γ-oryzanol and (B3) a carboxylic acid compound, the γ-oryzanol (A) being a mixture containing at least one ferulate ester of a vegetable sterol and at least one ferulate ester of a triterpene alcohol, and the hydrolysate of the γ-oryzanol (A) being a mixture containing at least one vegetable sterol and at least one triterpene alcohol.

DETAILED DESCRIPTION OF THE INVENTION

It has been found that a material containing a specific vegetable sterol, a triterpene alcohol derivative or a hydrogenated product thereof exhibits selective reflected color of from red to purple, more preferably from red to blue, especially in a temperature range around room temperature or body temperature, and thus shows high esthetic effect upon application on the human lips and skin as cosmetics. The invention has been completed based on the findings. The invention has the following features:

[1] A cholesteric liquid crystal composition containing at least one esterified product selected from the group consisting of:

(1) an esterified product of a hydrolysate of (A) a γ-oryzanol and (B1) a carboxylic acid compound, (2) an esterified product of a hydrogenated product of a hydrolysate of (A) a γ-oryzanol and (B2) a carboxylic acid compound, and (3) an esterified product of a hydrogenated product of (A) a γ-oryzanol and (B3) a carboxylic acid compound, the γ-oryzanol (A) being a mixture containing at least one ferulate ester of a vegetable sterol and at least one ferulate ester of a triterpene alcohol, and the hydrolysate of the γ-oryzanol (A) being a mixture containing at least one vegetable sterol and at least one triterpene alcohol.

[2] The cholesteric liquid crystal composition as described in item [1], wherein the carboxylic acid compound (B1) and the carboxylic acid compound (B2) are each independently a linear or branched and saturated or unsaturated aliphatic carboxylic acid compound having from 3 to 18 carbon atoms, a carboxylic acid compound represented by the following formula (b1) or a carboxylic acid compound represented by the following formula (b2), and the carboxylic acid compound (B3) is a linear or branched and saturated or unsaturated aliphatic carboxylic acid compound having from 3 to 18 carbon atoms:

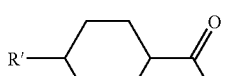

(b1)

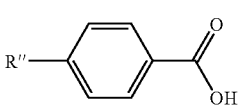

(b2)

wherein R' and R" each independently represents linear alkyl or alkoxy having from 1 to 8 carbon atoms.

[3] The cholesteric liquid crystal composition as described in item [1] or [2], wherein the γ-oryzanol (A) is a mixture that contains at least one compound represented by the formula (a1) and at least one compound represented by the formula (a2):

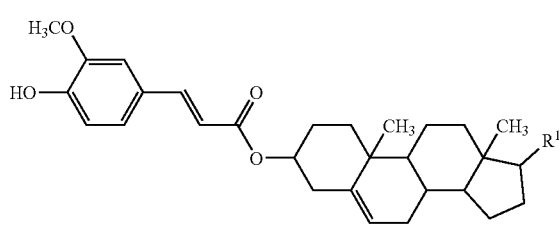

(a1)

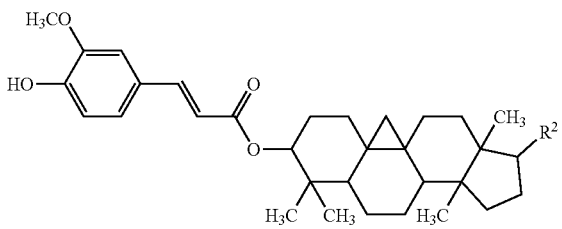

(a2)

wherein $R^1$ represents branched alkyl or alkenyl having from 9 to 10 carbon atoms, and $R^2$ represents branched alkyl or alkenyl having from 8 or 9 carbon atoms.

[4] The cholesteric liquid crystal composition as described in one of items [1] to [3], wherein the hydrolysate of the γ-oryzanol (A) is a mixture that contains at least one vegetable sterol selected from compounds represented by the formulae (a1-1) to (a1-4), and at least one triterpene alcohol selected from compounds represented by the formulae (a2-1) to (a2-4):

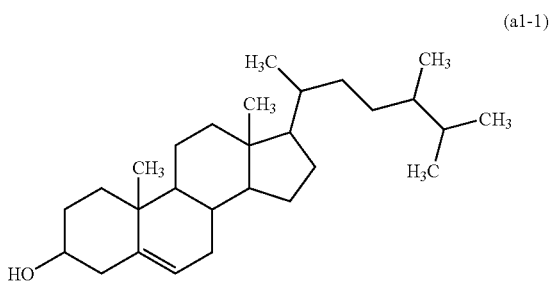

(a1-1)

(a1-2)

(a1-3)

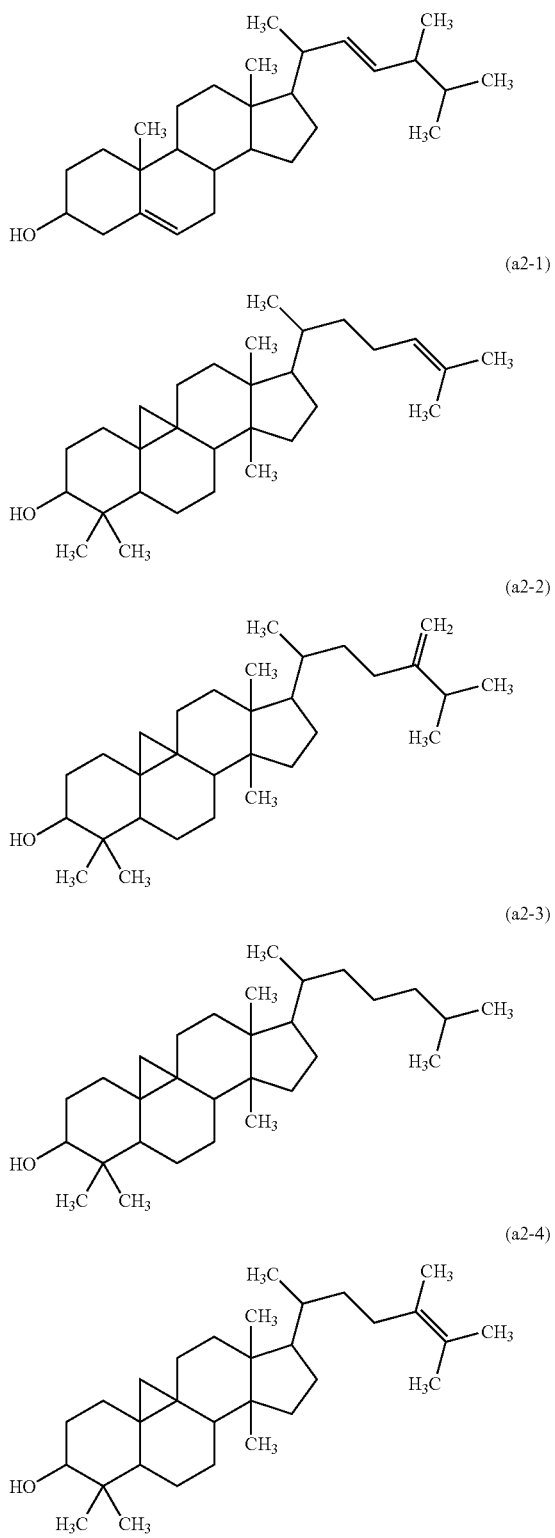

[5] The cholesteric liquid crystal composition as described in one of items [1] to [4], wherein the cholesteric liquid crystal composition contains two or more esterified products selected from the group consisting of the esterified product (1), the esterified product (2) and the esterified product (3).

[6] The cholesteric liquid crystal composition as described in item [2], wherein
the cholesteric liquid crystal composition contains the esterified product (1), the esterified product (2) and the esterified product (3),
the esterified product (1) is an esterified product of the hydrolysate of the γ-oryzanol (A) and the linear or branched and saturated or unsaturated aliphatic carboxylic acid compound having from 3 to 18 carbon atoms,
the esterified product (2) is an esterified product of the hydrogenated product of the hydrolysate of the γ-oryzanol (A) and the carboxylic acid compound represented by the formula (b1), and
the esterified product (3) is an esterified product of the hydrogenated product of the γ-oryzanol (A) and the linear or branched and saturated or unsaturated aliphatic carboxylic acid compound having from 3 to 18 carbon atoms.

[7] The cholesteric liquid crystal composition as described in item [2], wherein
the cholesteric liquid crystal composition contains the esterified product (1) and the esterified product (3),
the esterified product (1) contains an esterified product of the hydrolysate of the γ-oryzanol (A) and the carboxylic acid compound represented by the formula (b1), and an esterified product of the hydrolysate of the γ-oryzanol (A) and the linear or branched and saturated or unsaturated aliphatic carboxylic acid compound having from 3 to 18 carbon atoms, and
the esterified product (3) contains an esterified product of the hydrogenated product of the γ-oryzanol (A) and the linear or branched and saturated or unsaturated aliphatic carboxylic acid compound having from 3 to 18 carbon atoms.

[8] The cholesteric liquid crystal composition as described in item [2], wherein
the cholesteric liquid crystal composition contains the esterified product (2) and the esterified product (3),
the esterified product (2) contains an esterified product of the hydrogenated product of the hydrolysate of the γ-oryzanol (A) and the carboxylic acid compound represented by the formula (b1), and an esterified product of the hydrogenated product of the hydrolysate of the γ-oryzanol (A) and the linear or branched and saturated or unsaturated aliphatic carboxylic acid compound having from 3 to 18 carbon atoms, and
the esterified product (3) contains an esterified product of the hydrogenated product of the γ-oryzanol (A) and the linear or branched and saturated or unsaturated aliphatic carboxylic acid compound having from 3 to 18 carbon atoms.

[9] The cholesteric liquid crystal composition as described in item [2], wherein at least one of the carboxylic acid compound (B1), the carboxylic acid compound (B2) and the carboxylic acid compound (B3) is the linear or branched and saturated or unsaturated aliphatic carboxylic acid compound having 18 carbon atoms.

[10] The cholesteric liquid crystal composition as described in item [2], wherein the carboxylic acid compound (B1) is the linear or branched and saturated or unsaturated aliphatic carboxylic acid compound having 18 carbon atoms.

[11] The cholesteric liquid crystal composition as described in item [2], wherein the carboxylic acid compound (B2) is the linear or branched and saturated or unsaturated aliphatic carboxylic acid compound having 18 carbon atoms.

[12] The cholesteric liquid crystal composition as described in item [2], wherein the carboxylic acid compound (B3) is the linear or branched and saturated or unsaturated aliphatic carboxylic acid compound having 18 carbon atoms.

[13] The cholesteric liquid crystal composition as described in one of items [1] to [12], wherein the cholesteric liquid crystal composition further contains (4) an esterified product of the γ-oryzanol (A) and (B4) a carboxylic acid compound, wherein the carboxylic acid compound (B4) is a linear or branched and saturated or unsaturated aliphatic carboxylic acid compound having from 3 to 18 carbon atoms.

[14] The cholesteric liquid crystal composition as described in one of items [1] to [13], wherein the cholesteric liquid crystal composition further contains (5) an esterified product of a vegetable sterol extracted from soybean and (B5) a carboxylic acid compound.

[15] The cholesteric liquid crystal composition as described in item [14], wherein the carboxylic acid compound (B5) is a linear or branched and saturated or unsaturated aliphatic carboxylic acid compound having from 3 to 18 carbon atoms, a carboxylic acid compound represented by the following formula (b3) or a carboxylic acid compound represented by the following formula (b4):

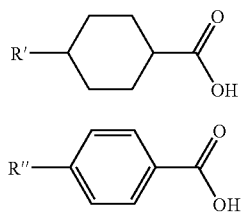

wherein R' and R" each independently represents linear alkyl or alkoxy having from 1 to 8 carbon atoms.

[16] The cholesteric liquid crystal composition as described in one of items [1] to [15], wherein the γ-oryzanol (A) contains the ferulate ester of a triterpene alcohol in an amount of 60% by weight or more.

[17] The cholesteric liquid crystal composition as described in one of items [1] to [16], wherein the cholesteric liquid crystal composition further contains at least one solvent selected from the group consisting of a fatty acid ester, a hydrocarbon, a higher alcohol, a lower alcohol, a polyhydric alcohol, a silicone oil, a cyclic ether, a ketone, an amide, an amino acid and an organic amine.

[18] A microcapsule comprising a core material containing the cholesteric liquid crystal composition as described in one of items [1] to [17], covered with a shell material.

[19] Use of the cholesteric liquid crystal composition as described in one of items [1] to [17] as one selected from the group consisting of a liquid crystal pigment, a paint, a spray ink, a printing ink, cosmetics, an anticounterfeit printed matter and an ornament.

[20] Cosmetics comprising the cholesteric liquid crystal composition as described in one of items [1] to [17].

[21] The cosmetics as described in item [20], wherein the cosmetics further contain at least one selected from the group consisting of a body pigment, a colorant, an antioxidant, an antioxidation assistant, an ultraviolet ray absorbent, a sequestering agent, a surfactant, a storage stabilizer, an antiseptic, a diluent, a plasticizer, a moisturizing agent, a viscosity controlling agent, a feel improver, a thickener, a film-forming agent, an ester oil, a liquid oil or fat, a solid oil or fat, wax, a water-soluble polymer, a cyclic ether, a ketone, an amide, an amino acid, an organic amine, a polyhydric alcohol, a polysaccharide, a polymer emulsion, a pH controlling agent, a vitamin, a skin nutrient, a perfume, an extract and water.

According to an aspect of the invention, such a liquid crystal composition can be provided that contains a vegetable raw material, has a cholesteric phase around room temperature or body temperature, can be controlled in reflected color in the cholesteric reflection region over a wide range of from red, green, blue to purple around room temperature or body temperature by changing the formulation of the composition, and exhibits esthetic effect upon application on the human lips and skin as cosmetics, and cosmetics containing the liquid crystal composition can also be provided.

The cholesteric liquid crystal composition according to an aspect of the invention and the purpose thereof are described in detail below.

In the following description, a compound represented by the formula (a1) may be referred to as "compound (a1)", and the rule may be applied to compounds represented by the other formulae. The expression "a linear or branched and saturated or unsaturated aliphatic carboxylic acid compound having from 3 to 18 carbon atoms", for example, means "a linear and saturated aliphatic carboxylic acid compound having from 3 to 18 carbon atoms", "a linear and unsaturated aliphatic carboxylic acid compound having from 3 to 18 carbon atoms", "a branched and saturated aliphatic carboxylic acid compound having from 3 to 18 carbon atoms" or "a branched and unsaturated aliphatic carboxylic acid compound having from 3 to 18 carbon atoms", and the rule may be applied to all the similar expressions.

[Cholesteric Liquid Crystal Composition]

The cholesteric liquid crystal composition of the invention (which may be referred simply to as "liquid crystal composition of the invention") contains at least one esterified product selected from the group containing (1) an esterified product of a hydrolysate of (A) a γ-oryzanol and (B1) a carboxylic acid compound, (2) an esterified product of a hydrogenated product of a hydrolysate of (A) a γ-oryzanol and (B2) a carboxylic acid compound, and (3) an esterified product of a hydrogenated product of (A) a γ-oryzanol and (B3) a carboxylic acid compound.

The liquid crystal composition of the invention has a wide cholesteric liquid crystal phase range around room temperature (approximately from 10° C. to 40° C.), and can be controlled in wavelength range of light reflected by the cholesteric phase by changing the kinds and ratios of the formulation of the constitutional components of the composition.

The γ-oryzanol (A) is a vegetable raw material obtained from rice bran, and a commercially available product thereof is a mixture that contains, as major components, at least one ferulate ester of a vegetable sterol and at least one ferulate ester of a triterpene alcohol, more specifically, a mixture that contains at least one compound represented by the formula (a1) and at least one compound represented by the formula (a2):

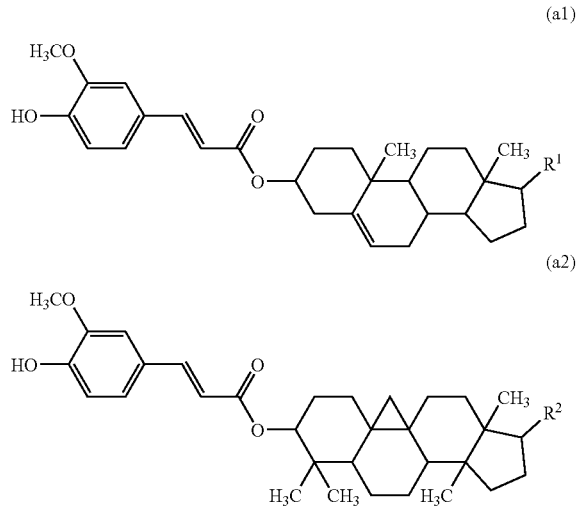

In the formulae (a1) and (a2), $R^1$ represents branched alkyl or alkenyl having from 9 to 10 carbon atoms, and $R^2$ represents branched alkyl or alkenyl having from 8 or 9 carbon atoms.

Examples of the compound (a1) include the following compounds.
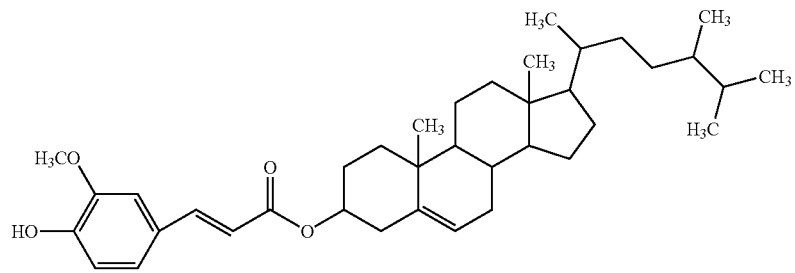
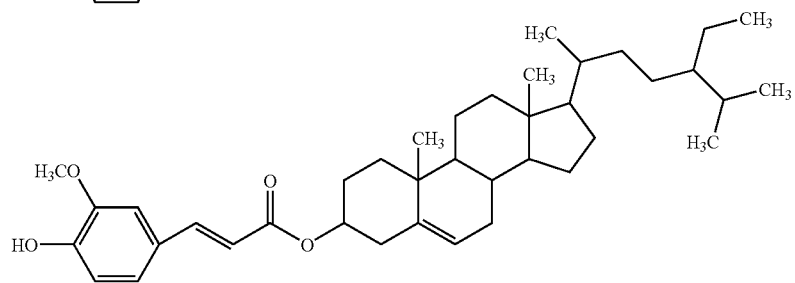
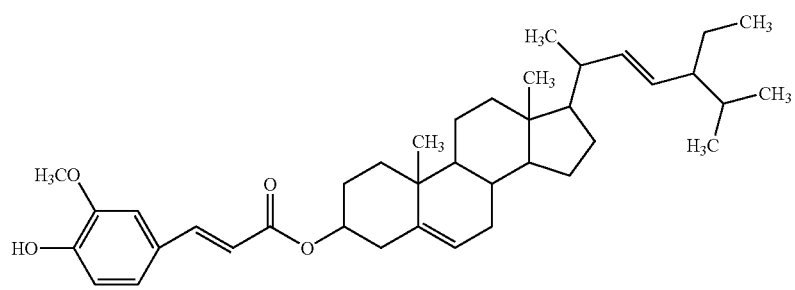
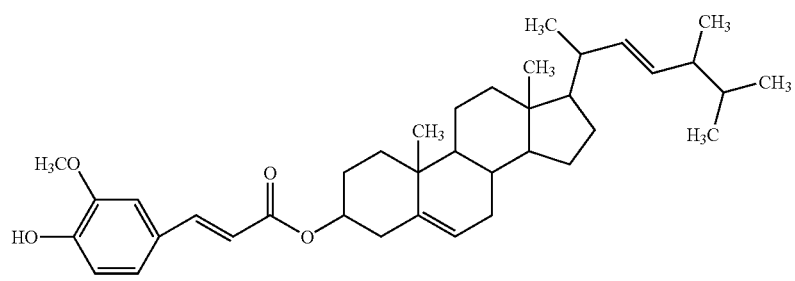
Examples of the compound (a2) include the following compounds.
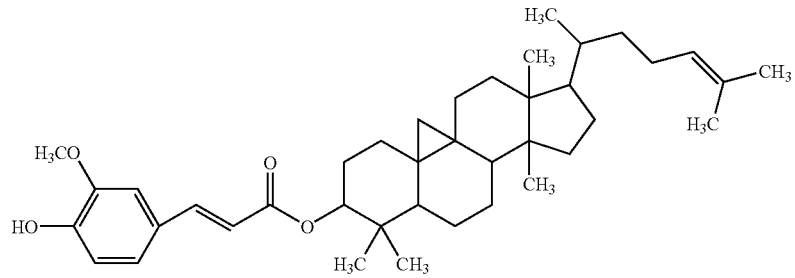

-continued

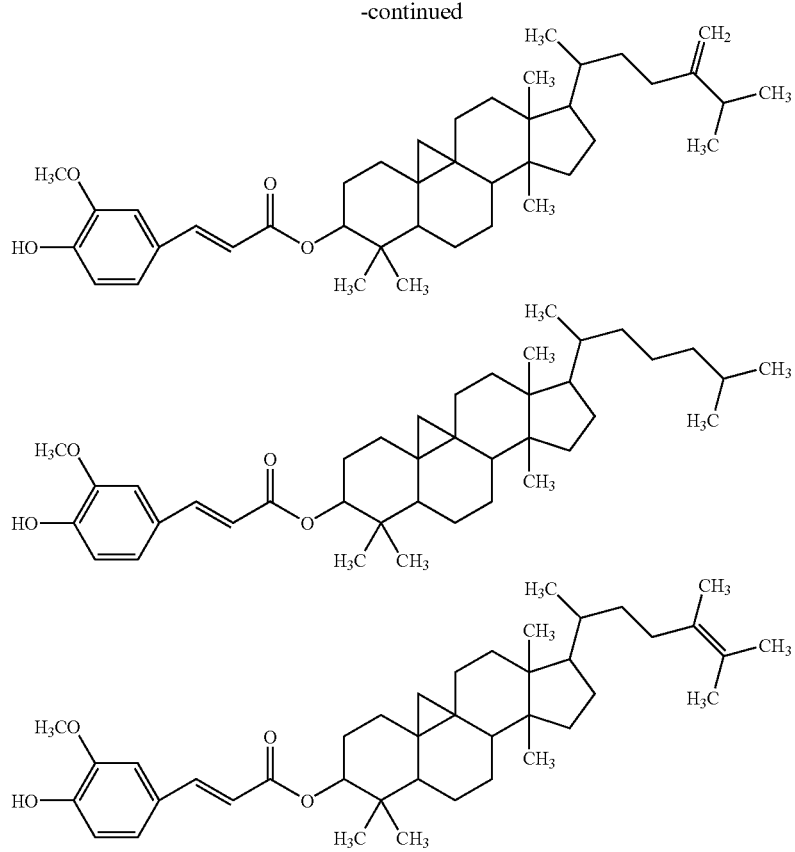

The γ-oryzanol (A) generally contains, as major components, two or three components selected from the examples of the compound (a1) and two or three components selected from the examples of the compound (a2), and the constitutional components and the compositional ratios thereof may vary depending on the suppliers of the raw materials used. The γ-oryzanol (A) may contain, as minor components, the example compounds other than the major components, and an isomer other than the example compounds.

The γ-oryzanol (A) preferably contains the ferulate ester of a triterpene alcohol in an amount of 60% by weight or more, more preferably 70% by weight or more, and particularly preferably 80% by weight or more, and in an amount of 99% by weight or less, more preferably 95% by weight or less, and particularly preferably 90% by weight or less.

A commercially available product may be used as the γ-oryzanol (A), and examples of the commercially available product include those available from Wako Pure Chemical Industries, Ltd., Tsuno Food Industrial Co., Ltd., Tsuno Rice Fine Chemicals Co., Ltd., Riken Vitamin Co., Ltd., Oryza Oil & Fat Chemical Co., Ltd. and Okayasu Shoten Co., Ltd.

The hydrolysate of the γ-oryzanol (A) is obtained by hydrolyzing the γ-oryzanol (A) and is a mixture that contains at least one, preferably two or more, vegetable sterol and at least one, preferably two or more, triterpene alcohol.

The γ-oryzanol (A) may be hydrolyzed according to a known method under known conditions. Specifically, for example, a mixture of a ferulate salt, a vegetable sterol and a triterpene alcohol is produced through reaction in such a manner that: an aqueous solution of potassium hydroxide or sodium hydroxide is added to the γ-oryzanol (A); the aqueous solution and a hydrophilic solvent, such as acetone, methanol, ethanol, propanol or tetrahydrofuran, are simultaneously added to the γ-oryzanol (A); or a solution containing potassium hydroxide or sodium hydroxide dissolved in methanol, ethanol, propanol or the like is added to the γ-oryzanol (A). Subsequently, the mixture is subjected to extraction with an organic solvent, and the resulting extract is neutralized, washed with water and dried over anhydrous magnesium sulfate, followed by removing the organic solvent, thereby providing the target mixture of a vegetable sterol and a triterpene alcohol (hydrolysate).

Examples of the vegetable sterol as the hydrolysate of the γ-oryzanol (A) include the following compounds (a1-1) to (a1-4).

(a1-1)

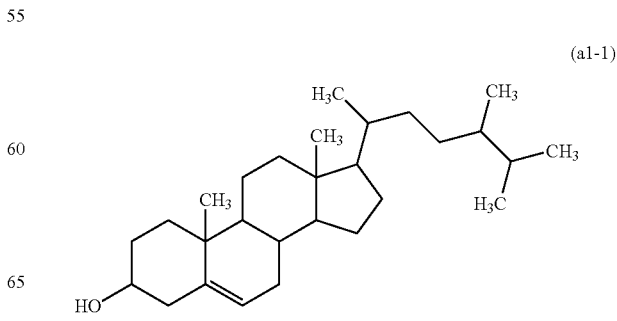

-continued

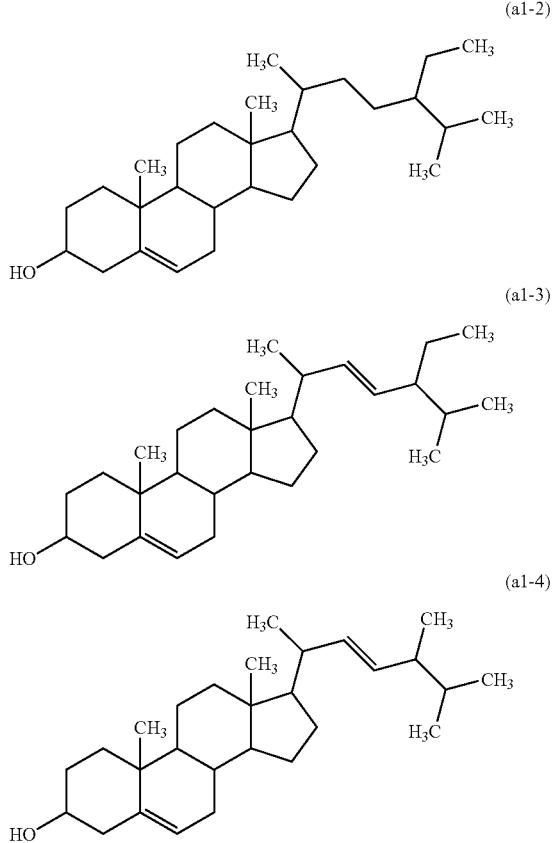

The hydrolysate may contain, as the vegetable sterol, an isomer other than the compounds (a1-1) to (a1-4).

Examples of the triterpene alcohol as the hydrolysate of the γ-oryzanol (A) include the following compounds (a2-1) to (a2-4).

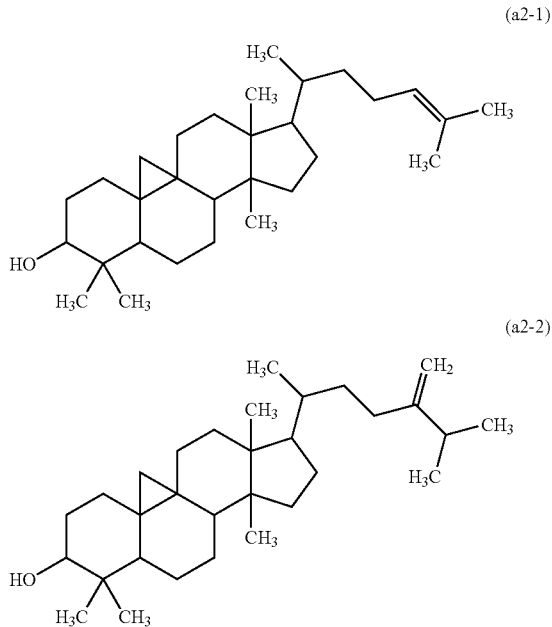

-continued

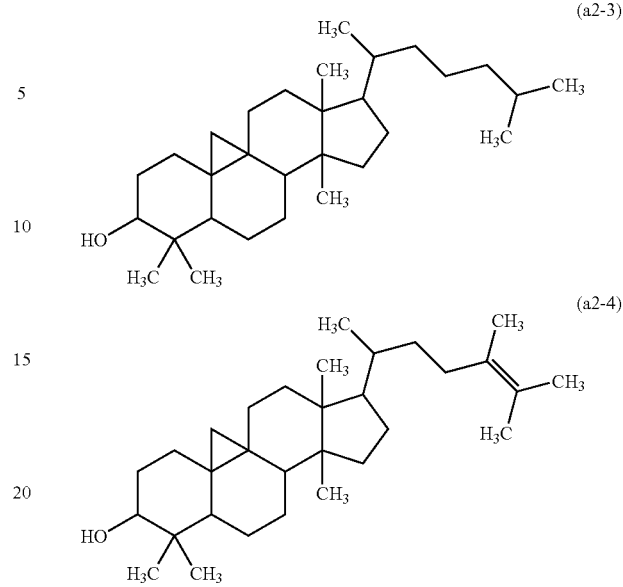

The hydrolysate may contain, as the triterpene alcohol, an isomer other than the compounds (a2-1) to (a2-4).

The hydrogenated product of the γ-oryzanol (A) and the hydrogenated product of the hydrolysate of the γ-oryzanol (A) can be obtained through hydrogenation according to a known method under known conditions. As a specific example of the method and conditions for hydrogenation, the γ-oryzanol (A) or the hydrolysate of the γ-oryzanol (A) is dissolved in an organic solvent, such as ethyl acetate, toluene or Solmix, to which activated carbon supporting palladium is added to perform catalytic hydrogenation reaction under ordinary pressure at room temperature. After completing the reaction, the reaction mixture is extracted with an organic solvent, washed with water and then dried over anhydrous magnesium sulfate, followed by removing the organic solvent, thereby providing the target hydrogenated product of the γ-oryzanol (A) or hydrogenated product of the hydrolysate of the γ-oryzanol (A).

The carboxylic acid compounds (B1) and (B2) are each independently a liner or branched and saturated or unsaturated aliphatic carboxylic acid compound having from 3 to 18 carbon atoms, a carboxylic acid compound represented by the following formula (b1) or a carboxylic acid compound represented by the following formula (b2). Among these, the compound (b1) is preferred since the compound has an effect of enhancing the region of the cholesteric phase of the composition. The liner or branched and saturated or unsaturated aliphatic carboxylic acid compound having from 3 to 18 carbon atoms preferably has from 6 to 18 carbon atoms, and more preferably from 8 to 13 or 18 carbon atoms. In the case where the carbon number is in the range, the composition can be relatively prevented from being crystallized, thereby enhancing the storage stability.

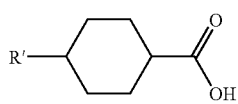

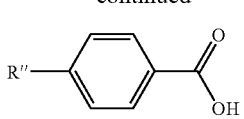

In the formulae (b1) and (b2), R' and R" each independently represents linear alkyl or alkoxy having from 1 to 8, preferably from 2 to 8, and more preferably from 3 to 6, carbon atoms. In the case where the carbon number of R' and R" is in the range, such an effect can be expected that the melting point of the composition is decreased, or the compatibility of the composition is increased, as compared to the case where the carbon number is outside the range.

The carboxylic acid compound (B3) is a linear or branched and saturated or unsaturated aliphatic carboxylic acid compound having from 3 to 18, preferably from 6 to 18, and more preferably from 8 to 13 or 18, carbon atoms. In the case where the carbon number is in the range, such an effect can be expected that the melting point of the composition is decreased, or the compatibility of the composition is increased.

The esterified product (1) of the hydrolysate of the γ-oryzanol (A) and the carboxylic acid compound (B1) can be obtained by subjecting the hydrolysate and the compound (B1) to esterification by a known method under known conditions. Examples of the method of esterification include a method of condensing a carboxylic acid and an alcohol in the presence of an acid catalyst, such as sulfuric acid and p-toluenesulfonic acid, or a condensing agent, such as dicyclohexylcarbodiimide (DCC), and a method of reacting an acid halide with an alcohol. Specifically, for example, a mixture of a vegetable sterol and a triterpene alcohol, which is the hydrolysate of the γ-oryzanol (A), is reacted with a chloride of the carboxylic acid compound (B1) in the presence of a tertiary amine, such as pyridine, triethylamine or N,N-dimethylaniline at room temperature. The reaction mixture is then extracted with an organic solvent, and the resulting extract is washed with water and then purified with column chromatography, thereby providing the target esterified product.

The esterified product (2) of the hydrogenated product of the hydrolysate of the γ-oryzanol (A) and the carboxylic acid compound (B2), and the esterified product (3) of the hydrogenated product of the γ-oryzanol (A) and the carboxylic acid compound (B3) can be obtained in the same manner under the same conditions as the esterified product (1).

The liquid crystal composition of the invention contains at least one, preferably two or more, esterified product selected from the group consisting of the esterified products (1), (2) and (3), whereby the composition has a wide cholesteric liquid crystal phase range around room temperature (approximately from 10° C. to 40° C.) and exhibits a helical pitch corresponding to an intended purpose.

Preferred examples of the combination of the esterified products (1), (2) and (3) include:

a combination containing
the esterified product (1) of the hydrolysate of the γ-oryzanol (A) and the linear or branched and saturated or unsaturated carboxylic acid compound having from 3 to 18 carbon atoms,
the esterified product (2) of the hydrogenated product of the hydrolysate of the γ-oryzanol (A) and the carboxylic acid compound represented by the formula (b1), and
the esterified product (3) of the hydrogenated product of the γ-oryzanol (A) and the linear or branched and saturated or unsaturated carboxylic acid compound having from 3 to 18 carbon atoms;

a combination containing
the esterified product (1) of the hydrolysate of the γ-oryzanol (A) and the carboxylic acid compound represented by the formula (b1),
the esterified product (1) of the hydrolysate of the γ-oryzanol (A) and the linear or branched and saturated or unsaturated carboxylic acid compound having from 3 to 18 carbon atoms, and
the esterified product (3) of the hydrogenated product of the γ-oryzanol (A) and the linear or branched and saturated or unsaturated carboxylic acid compound having from 3 to 18 carbon atoms;

a combination containing
the esterified product (2) of the hydrogenated product of the hydrolysate of the γ-oryzanol (A) and the carboxylic acid compound represented by the formula (b1),
the esterified product (2) of the hydrogenated product of the hydrolysate of the γ-oryzanol (A) and the linear or branched and saturated or unsaturated carboxylic acid compound having from 3 to 18 carbon atoms, and
the esterified product (3) of the hydrogenated product of the γ-oryzanol (A) and the linear or branched and saturated or unsaturated carboxylic acid compound having from 3 to 18 carbon atoms;

a combination containing
the esterified product (1) of the hydrolysate of the γ-oryzanol (A) and the carboxylic acid compound represented by the formula (b1), and
the esterified product (3) of the hydrogenated product of the γ-oryzanol (A) and the linear or branched and saturated or unsaturated carboxylic acid compound having from 3 to 18 carbon atoms; and a combination containing
the esterified product (2) of the hydrogenated product of the hydrolysate of the γ-oryzanol (A) and the carboxylic acid compound represented by the formula (b1), and
the esterified product (3) of the hydrogenated product of the γ-oryzanol (A) and the linear or branched and saturated or unsaturated carboxylic acid compound having from 3 to 18 carbon atoms.

At least one of the carboxylic acid compound (B1), the carboxylic acid compound (B2) and the carboxylic acid compound (B3) is preferably a linear or branched and saturated or unsaturated aliphatic carboxylic acid compound having 18 carbon atoms. In the case where the carbon number is 18, such an effect is expected that the melting point of the composition is further decreased, or the composition is relatively prevented from being crystallized to further enhance the storage stability.

The liquid crystal composition of the invention may further contain (4) an esterified product of the γ-oryzanol (A) and (B4) a carboxylic acid compound.

The carboxylic acid compound (B4) is a linear or branched and saturated or unsaturated aliphatic carboxylic acid compound having from 3 to 18, preferably from 6 to 18, and more preferably from 8 to 13 or 18, carbon atoms. In the case where the carbon number is in the range, such an effect is expected that the melting point of the composition is further decreased, or the compatibility of the composition is further increased, as compared to the case where the carbon number is outside the range.

The esterified product (4) of the γ-oryzanol (A) and the carboxylic acid compound (B4) can be obtained in the same manner under the same conditions as the esterified product (1).

In the liquid crystal composition of the invention, the esterified product (4) may be contained in an amount of from 0 to 40 parts by weight, preferably from 5 to 30 parts by weight, and more preferably from 5 to 20 parts by weight, per 100 parts by weight in total of the esterified products (1), (2) and (3). In the case where the esterified product (4) is contained in an amount within the range, the cholesteric phase of the resulting liquid crystal composition can be controlled.

The liquid crystal composition of the invention may further contain (5) an esterified product of a vegetable sterol extracted from soybean and (B5) a carboxylic acid compound.

Examples of the vegetable sterol extracted from soybean include β-sitosterol, campesterol and stigmasterol, which are available as an isolated product or a mixture. Examples thereof include those available from Tama Biochemical Co., Ltd., Tokyo Chemical Industry Co., Ltd. and Sigma-Ardrich Japan Co., Ltd.

The carboxylic acid compound (B5) is a linear or branched and saturated or unsaturated aliphatic carboxylic acid compound having from 3 to 18 carbon atoms, a carboxylic acid compound represented by the following formula (b3) or a carboxylic acid compound represented by the following formula (b4), and is preferably the compound (b3). The linear or branched and saturated or unsaturated aliphatic carboxylic acid compound having from 3 to 18 carbon atoms preferably has from 6 to 18 carbon atoms, and more preferably from 8 to 18 carbon atoms. In the case where the carbon number is in the range, the composition can be relatively prevented from being crystallized, thereby enhancing the storage stability.

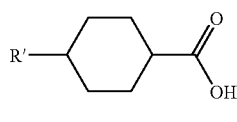

(b3)

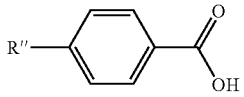

(b4)

In the formulae (b3) and (b4), R' and R" each independently represents linear alkyl or alkoxy having from 1 to 8, preferably from 3 to 5, carbon atoms.

The esterified product (5) of the vegetable sterol extracted from soybean and the carboxylic acid compound (B5) can be obtained by subjecting the vegetable sterol and the carboxylic acid compound (B5) to esterification by a known method under known conditions.

In the liquid crystal composition of the invention, the esterified product (5) may be contained in an amount of from 0 to 40 parts by weight, preferably from 5 to 30 parts by weight, and more preferably from 5 to 20 parts by weight, per 100 parts by weight in total of the esterified products (1), (2) and (3). In the case where the esterified product (5) is contained in an amount within the range, the composition can be relatively prevented from being crystallized, thereby enhancing the storage stability.

The liquid crystal composition of the invention may further contain other components in such a range that does not impair the advantages of the invention. Examples of the other components include a vegetable-derived material other than the esterified products (1) to (5) (which may be referred to as "additional vegetable-derived material") and a solvent.

Specific examples of the additional vegetable-derived material include "Riceterol Ester", available from Tsuno Food Industrial Co., Ltd.

Examples of the solvent include a fatty acid ester (except for the aforementioned esterified products), a hydrocarbon, a higher alcohol, a lower alcohol, a polyhydric alcohol, a silicone oil, a cyclic ether, a ketone, an amide, an amino acid and an organic amine, which may be used solely or as a mixture of two or more of them.

[Uses]

The uses of the cholesteric liquid crystal composition of the invention include a general color material, such as a liquid crystal pigment, a paint, a spray ink, a printing ink and the like. The liquid crystal composition can also be used as cosmetics, an anticounterfeit printed matter, an ornament and the like. Among these, the liquid crystal composition can be favorably used as cosmetics since the composition exhibits selective reflected color of from red to purple, preferably from red to yellow, in a temperature range around room temperature or body temperature.

The cosmetics according to the invention contain the cholesteric liquid crystal composition of the invention. The cosmetics may further contain, in addition to the liquid crystal composition, within the range not damaging the effect of the invention, a component that is ordinarily used in cosmetics depending on purpose of use, such as a body pigment, a colorant, an antioxidant, an antioxidation assistant, an ultraviolet ray absorbent, a sequestering agent, a surfactant, a storage stabilizer, an antiseptic, a diluent, a plasticizer, a moisturizing agent, a viscosity controlling agent, a feel improver, a thickener, a film-forming agent, an ester oil, a liquid oil or fat, a solid oil or fat, wax, a water-soluble polymer, a cyclic ether, a ketone, an amide, an amino acid, an organic amine, a polyhydric alcohol, a polysaccharide, a polymer emulsion, a pH controlling agent, a vitamin, a skin nutrient, a perfume, various extracts and water.

Examples of the body pigment include barium sulfate, barium carbonate, calcium carbonate, magnesium carbonate, silica, titanium oxide, mica, sericite and talc, which may be used solely or in combination of two or more of them.

Examples of the colorant include those of such series as soluble azo, insoluble azo, polyazo, phthalocyanine, anthraquinone, thioindigo, perilene, perynone, dioxazine, quinacridone, isoindoline, quinophthalone, diketopyrrolopyrrole and carbon black.

Examples of the antioxidant include 2,2-methylenebis(4-methyl-6-t-butylphenol) and 2,6-di-t-butyl-4-methylphenol (BHT).

Examples of the ultraviolet ray absorbent include 2-(3-t-butyl-5-methyl-2-hydroxyphenyl)-5-chloro-benzotriazole and an alkoxybenzophenone compound.

Examples of the moisturizing agent include an animal oil, a vegetable oil and a synthetic oil without limitation in derivation and nature thereof, e.g., a solid oil, a semisolid oil, a liquid oil and a volatile oil, such as a hydrocarbon, an oil or fat, wax, a hydrogenated oil, an ester oil, a fatty acid, a lower alcohol, a glycol, a glycerol, a high alcohol, a silicone oil, a fluorine oil, a lanolin derivative and a vegetable sterol derivative.

Specific examples thereof include a hydrocarbon, such as liquid paraffin, squalene, vaseline, polyisobutylene, polybutene, paraffin wax, ceresin wax, microcrystalline wax, montan wax and Fischer-Tropsch wax; an oil or fat, such as haze wax, olive oil, castor oil, mink oil and macadamia nut oil; wax, such as bees wax, carnauba wax, candelilla wax and spermaceti wax; an ester oil, such as jojoba oil, cetyl isooctanoate, isopropyl myristate, isopropyl palmitate, octyldodecyl myristate, glyceryl trioctanoate, diglyceryl diisostearate, diglyceryl triisostearate, glyceryl tribehenate, pentaerythritol rosinate, neopentylglycol dioctanoate, a cholesterol fatty acid ester and di(cholesteryl-behenyl-octyldodecyl) N-lauroyl-L-glutamate; a fatty acid, such as stearic acid, lauric acid, myristic acid, behenic acid, isostearic acid, oleic acid and 12-hydroxystearic acid; a higher alcohol, such as stearyl alcohol, cetyl alcohol, lauryl alcohol, oleyl alcohol, isostearyl alcohol and behenyl alcohol; a silicone oil, such as low polymerization degree dimethylpolysiloxane, high polymerization degree dimethylpolysiloxane, methylphenylpolysiloxane, decamethylcyclopentasiloxane, octamethylcyclotetrasiloxane and fluorine-modified silicone; a fluorine oil, such as perfluoropolyether, perfluorodecane and perfluorooctane; a lanolin derivative, such as lanolin, acetylated lanolin, lanolin fatty acid isopropyl ester and lanolin alcohol; a sitosterol derivative; a campesterol derivative; a stigmasterol derivative; an alcohol, such as ethanol and isopropyl alcohol; a glycol, such as propylene glycol, 1,3-butylene glycol, dipropylene glycol and polyethylene glycol; a glycerol, such as glycerin, diglycerin and polyglycerin; and sorbit, which may be used solely or in combination of two or more of them.

Examples of the viscosity controlling agent and the feel improver include a vegetable-derived polymer (such as gum arabic, tragacanth gum, galactan, guar gum, carob gum, karaya gum, carrageen, pectin, agar, quince seed, algae colloid (brown algae extract), starch (derived from rice, corn, potato or wheat), glycyrrhizinic acid, hyaluronic acid and a hyaluronic acid derivative), a microorganism-derived polymer (such as xanthan gum, dextran, succinoglycan and pullulan), and an animal-derived polymer (such as collagen, casein, albumin and gelatin).

Examples of the semisynthetic water-soluble polymer include a starch polymer (such as carboxymethyl starch and methylhydroxypropyl starch); a cellulose polymer (such as methyl cellulose, ethyl cellulose, methylhydroxypropyl cellulose, hydroxyethyl cellulose, cellulose sodium sulfate, hydroxypropyl cellulose, carboxymethyl cellulose, sodium carboxymethyl cellulose, crystalline cellulose and cellulose powder); an alginic acid polymer (such as sodium alginate and alginic acid propylene glycol ester); and sodium hyaluronate.

Examples of the synthetic water-soluble polymer include a vinyl polymer (such as polyvinyl alcohol, polyvinyl methyl ether, polyvinylpyrrolidone and carboxyvinyl polymer); a polyoxyethylene polymer (such as a polyoxyethylene-polyoxypropylene copolymer, which is polyethylene glycol); an acrylic polymer (such as sodium polyacrylate, polyethyl acrylate and polyacrylamide); polyethyleneimine; and a cationic polymer.

Examples of the thickener include gum arabic, carrageen, karaya gum, tragacanth gum, carob gum, quince seed, casein, dextrin, gelatin, sodium pectinate, sodium alginate, methyl cellulose, ethyl cellulose, carboxymethyl cellulose (CMC), hydroxyethyl cellulose, hydroxypropyl cellulose, polyvinyl alcohol (PVA), polyvinyl methyl ether (PVM), polyvnylpyrrolidone (PVP), sodium polyacrylate, carboxyvinyl polymer, locust bean gum, guar gum, tamarind gum, dialkyldimethylammonium sulfate cellulose, xanthan gum, aluminum magnesium silicate, bentonite, hectorite, Veegum (aluminum magnesium silicate), laponite, silicic anhydride, sodium chondroitin sulfate, carboxyvinyl polymer and alkyl-modified carboxyvinyl polymer.

The cosmetics of the invention can be favorably used as a lipstick, a lipbalm, a lipgloss, an eyeshadow, an eyeliner, a mascara, a blusher, a liquid foundation and the like.

EXAMPLE

The invention will be described in more detail with reference to examples below, but the invention is not limited to the examples.

Synthesis Example 1

(1) A mixture containing 50.0 g of a γ-oryzanol, available from Okayasu Shoten Co., Ltd., 30 g (0.45 mol) of potassium hydroxide (85%) and 500 mL of ethanol was stirred under heating and refluxing for 10 hours. Ethanol was distilled off from the mixture, which was then extracted with ethyl acetate, and the extract was washed with a saturated sodium hydrogen carbonate aqueous solution and then with water. The solution was dried over magnesium sulfate, and the solvent was distilled off to provide a hydrolysate of the γ-oryzanol as a brown solid.

(2) 20 mL of thionyl chloride was added dropwise to a mixture containing 20.0 g (0.1 mol) of trans-4-pentylcyclohexanecarboxylic acid represented by the following formula (b-i), 0.5 mL of pyridine and 300 mL of toluene in a nitrogen atmosphere, and the mixture was stirred under heating to 80° C. or less for 1 hour. The solvent was distilled off under reduced pressure to provide trans-4-pentylcyclohexanecarboxylic acid chloride.

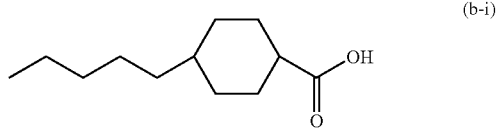

(b-i)

(3) 1.2 g (5 mmol) of the trans-4-pentyl-cyclohexanecarboxylic acid chloride obtained in the item (2) was added dropwise to a mixture containing 2.2 g (5 mmol) of the hydrolysate of the γ-oryzanol obtained in the item (1), 0.5 mL of pyridine, a slight amount of dimethylaminopyridine and 50 mL of toluene at room temperature, followed by stirring at room temperature for 4 hours. After completing the reaction, an insoluble matter thus deposited was removed by filtration, and the filtrate was washed with water and dried over magnesium sulfate, followed by distilling off the solvent. The resulting residue was purified with column chromatography (silica gel chromatography, eluent:toluene/heptane (volume ratio: 3/2)) to provide 2.0 g of an esterified product (1-1).

Synthesis Example 2

The γ-oryzanol was hydrolyzed in the same manner as in Synthesis Example 1. Oleic acid represented by the following formula (b-ii) was chlorinated in the same manner as in Synthesis Example 1 to provide oleic acid chloride.

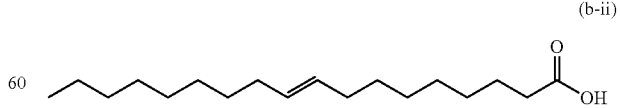

(b-ii)

3.6 g (12 mmol) of the oleic acid chloride was added dropwise to a mixture containing 4.4 g (10 mmol) of the hydrolysate, 1.0 mL of pyridine and 50 mL of toluene at room temperature, followed by stirring at room temperature for 3 hours. After completing the reaction, an insoluble matter thus deposited was removed by filtration, and the filtrate was washed with water and dried over magnesium sulfate, followed by distilling off the solvent. The resulting residue was purified with column chromatography (silica gel chromatography, eluent:toluene/heptane (volume ratio: 3/2)) to provide 4.0 g of an esterified product (1-2).

Synthesis Example 3

The γ-oryzanol was hydrolyzed in the same manner as in Synthesis Example 1. A mixture containing 2.2 g (5 mmol) of the resulting hydrolysate, 20 mL of toluene, 5 mL of Solmix and 0.1 g of activated carbon supporting 5% of palladium (5% Pd/C) was then stirred in a hydrogen atmosphere at room temperature for 6 hours. After completing the reaction, the activated carbon supporting palladium was removed by filtration, and the filtrate was washed with water and dried over magnesium sulfate, followed by distilling off the solvent, to provide a hydrogenated product of the hydrolysate of the γ-oryzanol. 2.0 g of the hydrogenated product of the hydrolysate and 1.0 g of trans-4-pentylcyclohexanecarboxylic acid represented by the following formula (b-i) were subjected to esterification in the same manner under the same conditions as in Synthesis Example 1 to provide 1.8 g of an esterified product (2-1).

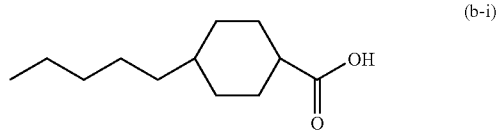
(b-i)

Synthesis Example 4

4.4 g (10 mol) of the hydrogenated product of the hydrolysate of the γ-oryzanol obtained in the same manner as in Synthesis Example 3 and 3.3 g of oleic acid represented by the following formula (b-ii) were subjected to esterification in the same manner under the same conditions as in Synthesis Example 2 to provide 3.6 g of an esterified product (2-2).

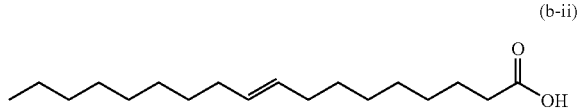
(b-ii)

Synthesis Example 5

A mixture containing 6.2 g (10 mmol) of a γ-oryzanol, 30 mL of toluene, 10 mL of Solmix and 0.3 g of activated carbon supporting 5% of palladium (5% Pd/C) was stirred in a hydrogen atmosphere at room temperature for 6 hours. After completing the reaction, the activated carbon supporting palladium was removed by filtration, and the filtrate was washed with water and dried over magnesium sulfate, followed by distilling off the solvent, to provide a hydrogenated product of the γ-oryzanol. 5.8 g of the hydrogenated product of the γ-oryzanol and 3.1 g of oleic acid represented by the following formula (b-ii) were subjected to esterification in the same manner under the same conditions as in Synthesis Example 2 to provide 4.8 g of an esterified product (3-1).

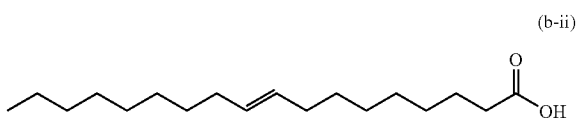
(b-ii)

Synthesis Example 6

A hydrogenated product of the γ-oryzanol was obtained in the same manner as in Synthesis Example 5. 6.2 g (10 mmol) of the hydrogenated product of the γ-oryzanol and 1.9 g of decanoic acid represented by the following formula (b-iii) were subjected to esterification in the same manner under the same conditions as in Synthesis Example 2 to provide 5.0 g of an esterified product (3-2).

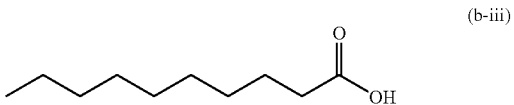
(b-iii)

Example 1

30 parts by weight of the esterified product (1-2), 40 parts by weight of the esterified product (2-1) and 30 parts by weight of the esterified product (3-1) were mixed to prepare a liquid crystal composition. The resulting composition showed green reflected color at room temperature, showed green to orange reflected color at 35° C., and showed green to orange reflected color at 40° C. The reflected color was determined by visual observation. The results are shown in Table 1.

Examples 2 to 9

Compositions having the formulations shown in Table 1 were prepared and evaluated for reflected color in the same manner as in Example 1. The results are shown in Table 1.

TABLE 1

| | | Example | | | | | | | | |
|---|---|---|---|---|---|---|---|---|---|---|
| | | 1 | 2 | 3 | 4 | 5 | 6 | 7 | 8 | 9 |
| Formulation (part by weight) | Esterified product (1-1) | — | — | — | 45 | 32 | 34 | — | — | — |
| | Esterified product (1-2) | 30 | 20 | 25 | 30 | 21 | 17 | — | — | — |
| | Esterified product (2-1) | 40 | 40 | 35 | — | — | — | 32 | 33 | 40 |

TABLE 1-continued

| | | Example | | | | | | | | |
|---|---|---|---|---|---|---|---|---|---|---|
| | | 1 | 2 | 3 | 4 | 5 | 6 | 7 | 8 | 9 |
| | Esterified product (2-2) | — | — | — | — | — | — | 26 | 33 | 20 |
| | Esterified product (3-1) | 30 | 40 | 40 | 25 | 47 | 49 | 42 | 33 | 40 |
| Reflected color | Room temperature | green | green | green | green | green | green | green | green | green |
| | 35° C. | green to orange | vermilion | orange | green | orange | green | orange | green | vermilion |
| | 40° C. | green to orange | red | red | green | red | red | red | orange | red |

Example 10

41 parts by weight of the esterified product (2-1), 31 parts by weight of the esterified product (3-2) and 28 parts by weight of "Ricetrol Ester", available from Tsuno Food Industrial Co., Ltd., were mixed to provide a liquid crystal composition. The resulting composition showed green reflected color at room temperature, showed orange reflected color at 35° C., and showed red reflected color at 40° C. The results are shown in Table 2.

Example 11

A composition having the formulation shown in Table 2 was prepared and evaluated for reflected color in the same manner as in Example 10. The results are shown in Table 2.

TABLE 2

| | | Example | |
|---|---|---|---|
| | | 10 | 11 |
| Formulation (part by weight) | Esterified product (1-1) | — | 45 |
| | Esterified product (2-1) | 41 | — |
| | Esterified product (3-2) | 31 | 38 |
| | Ricetrol Ester*1 | 28 | 17 |
| Reflected color | Room temperature | green | green |
| | 35° C. | orange | red |
| | 40° C. | red | red |

*1"Ricetrol Ester", available from Tsuno Food Industrial Co., Ltd.

What is claimed is:

1. A cholesteric liquid crystal composition containing at least one esterified product selected from the group consisting of:
   (1) an esterified product of a hydrolysate of (A) a γ-oryzanol and (B1) a carboxylic acid compound,
   (2) an esterified product of a hydrogenated product of a hydrolysate of (A) a γ-oryzanol and (B2) a carboxylic acid compound, and
   (3) an esterified product of a hydrogenated product of (A) a γ-oryzanol and (B3) a carboxylic acid compound,
   the γ-oryzanol (A) being a mixture containing at least one ferulate ester of a vegetable sterol and at least one ferulate ester of a triterpene alcohol, and
   the hydrolysate of the γ-oryzanol (A) being a mixture containing at least one vegetable sterol and at least one triterpene alcohol.

2. The cholesteric liquid crystal composition as claimed in claim 1, wherein
   the carboxylic acid compound (B1) and the carboxylic acid compound (B2) are each independently a linear or branched and saturated or unsaturated aliphatic carboxylic acid compound having from 3 to 18 carbon atoms, a carboxylic acid compound represented by the following formula (b1) or a carboxylic acid compound represented by the following formula (b2), and
   the carboxylic acid compound (B3) is a linear or branched and saturated or unsaturated aliphatic carboxylic acid compound having from 3 to 18 carbon atoms:

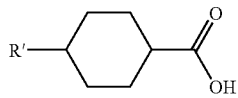

(b1)

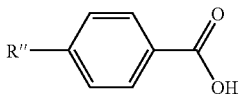

(b2)

wherein R' and R'' each independently represents linear alkyl or alkoxy having from 1 to 8 carbon atoms.

3. The cholesteric liquid crystal composition as claimed in claim 1, wherein the γ-oryzanol (A) is a mixture that contains at least one compound represented by the formula (a1) and at least one compound represented by the formula (a2):

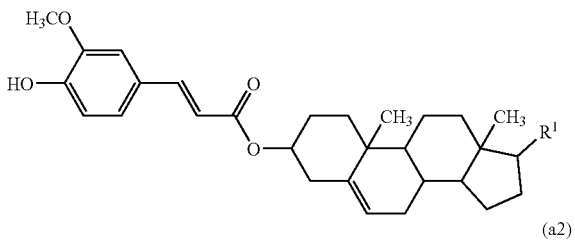

(a1)

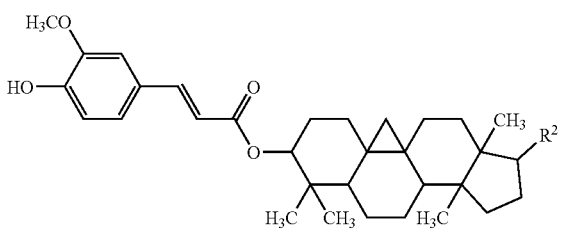

(a2)

wherein $R^1$ represents branched alkyl or alkenyl having from 9 to 10 carbon atoms, and $R^2$ represents branched alkyl or alkenyl having from 8 or 9 carbon atoms.

4. The cholesteric liquid crystal composition as claimed in claim 1, wherein the hydrolysate of the γ-oryzanol (A) is a mixture that contains at least one vegetable sterol selected from compounds represented by the formulae (a1-1) to (a1-4), and at least one triterpene alcohol selected from compounds represented by the formulae (a2-1) to (a2-4):

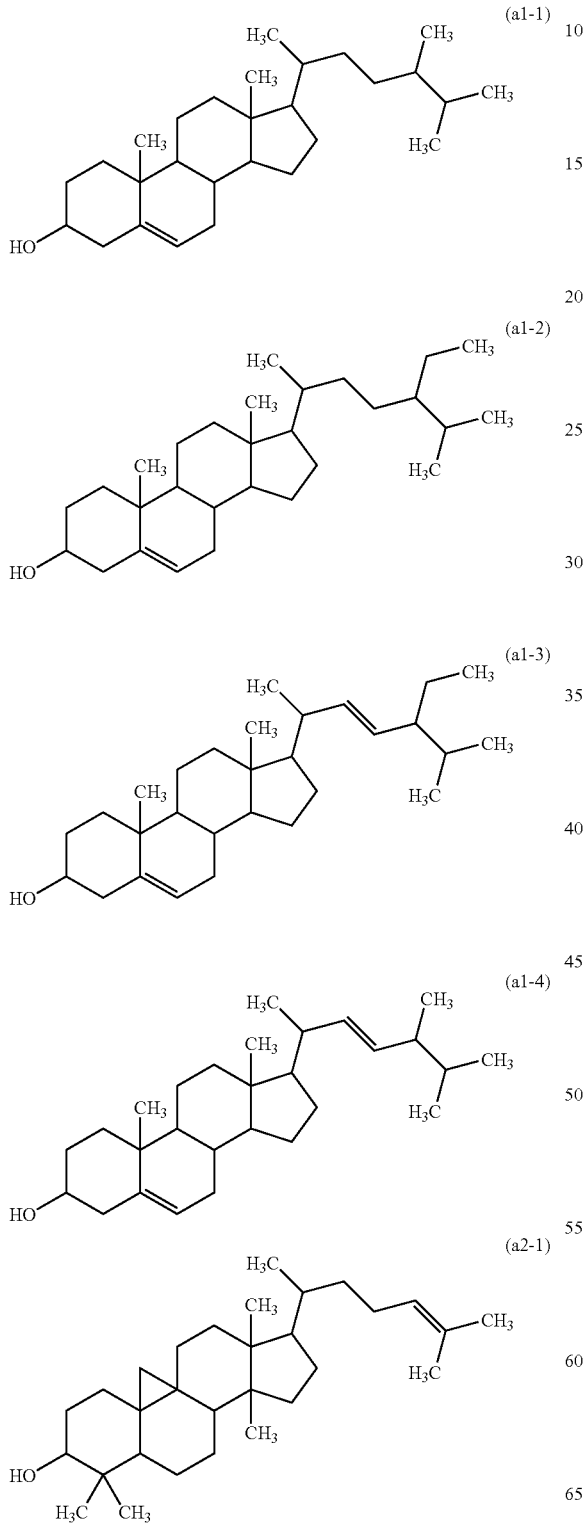

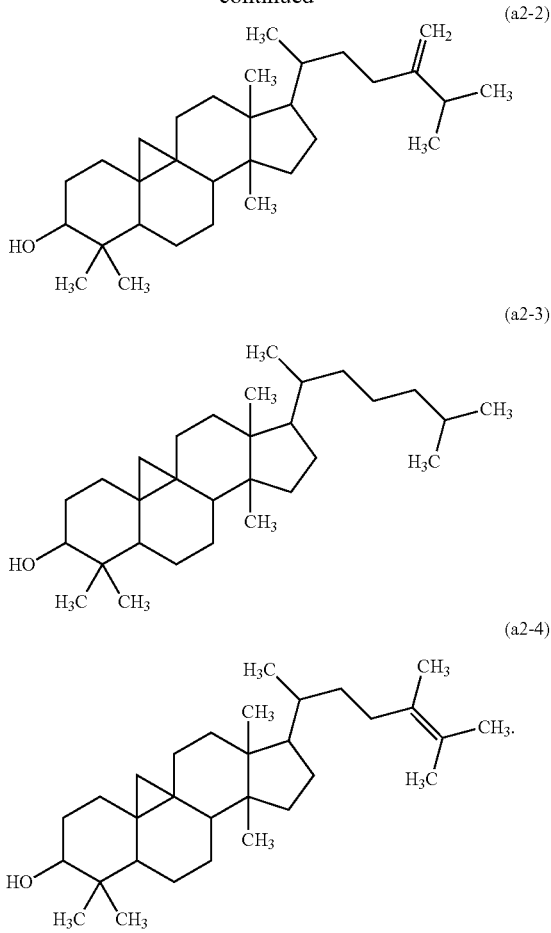

5. The cholesteric liquid crystal composition as claimed in claim 1, wherein the cholesteric liquid crystal composition contains two or more esterified products selected from the group consisting of the esterified product (1), the esterified product (2) and the esterified product (3).

6. The cholesteric liquid crystal composition as claimed in claim 2, wherein
the cholesteric liquid crystal composition contains the esterified product (1), the esterified product (2) and the esterified product (3),
the esterified product (1) is an esterified product of the hydrolysate of the γ-oryzanol (A) and the linear or branched and saturated or unsaturated aliphatic carboxylic acid compound having from 3 to 18 carbon atoms,
the esterified product (2) is an esterified product of the hydrogenated product of the hydrolysate of the γ-oryzanol (A) and the carboxylic acid compound represented by the formula (b1), and
the esterified product (3) is an esterified product of the hydrogenated product of the γ-oryzanol (A) and the linear or branched and saturated or unsaturated aliphatic carboxylic acid compound having from 3 to 18 carbon atoms.

7. The cholesteric liquid crystal composition as claimed in claim 2, wherein
the cholesteric liquid crystal composition contains the esterified product (1) and the esterified product (3),
the esterified product (1) contains an esterified product of the hydrolysate of the γ-oryzanol (A) and the carboxylic acid compound represented by the formula (b1), and an esterified product of the hydrolysate of the γ-oryzanol (A) and the linear or branched and saturated or unsaturated aliphatic carboxylic acid compound having from 3 to 18 carbon atoms, and the esterified product (3) contains an esterified product of the hydrogenated product of the γ-oryzanol (A) and the linear or branched and saturated or unsaturated aliphatic carboxylic acid compound having from 3 to 18 carbon atoms.

8. The cholesteric liquid crystal composition as claimed in claim 2, wherein the cholesteric liquid crystal composition contains the esterified product (2) and the esterified product (3), the esterified product (2) contains an esterified product of the hydrogenated product of the hydrolysate of the γ-oryzanol (A) and the carboxylic acid compound represented by the formula (b1), and an esterified product of the hydrogenated product of the hydrolysate of the γ-oryzanol (A) and the linear or branched and saturated or unsaturated aliphatic carboxylic acid compound having from 3 to 18 carbon atoms, and the esterified product (3) contains an esterified product of the hydrogenated product of the γ-oryzanol (A) and the linear or branched and saturated or unsaturated aliphatic carboxylic acid compound having from 3 to 18 carbon atoms.

9. The cholesteric liquid crystal composition as claimed in claim 2, wherein at least one of the carboxylic acid compound (B1), the carboxylic acid compound (B2) and the carboxylic acid compound (B3) is the linear or branched and saturated or unsaturated aliphatic carboxylic acid compound having 18 carbon atoms.

10. The cholesteric liquid crystal composition as claimed in claim 2, wherein the carboxylic acid compound (B1) is the linear or branched and saturated or unsaturated aliphatic carboxylic acid compound having 18 carbon atoms.

11. The cholesteric liquid crystal composition as claimed in claim 2, wherein the carboxylic acid compound (B2) is the linear or branched and saturated or unsaturated aliphatic carboxylic acid compound having 18 carbon atoms.

12. The cholesteric liquid crystal composition as claimed in claim 2, wherein the carboxylic acid compound (B3) is the linear or branched and saturated or unsaturated aliphatic carboxylic acid compound having 18 carbon atoms.

13. The cholesteric liquid crystal composition as claimed in claim 1, wherein the cholesteric liquid crystal composition further contains (4) an esterified product of the γ-oryzanol (A) and (B4) a carboxylic acid compound, wherein the carboxylic acid compound (B4) is a linear or branched and saturated or unsaturated aliphatic carboxylic acid compound having from 3 to 18 carbon atoms.

14. The cholesteric liquid crystal composition as claimed in claim 1, wherein the cholesteric liquid crystal composition further contains (5) an esterified product of a vegetable sterol extracted from soybean and (B5) a carboxylic acid compound.

15. The cholesteric liquid crystal composition as claimed in claim 14, wherein the carboxylic acid compound (B5) is a linear or branched and saturated or unsaturated aliphatic carboxylic acid compound having from 3 to 18 carbon atoms, a carboxylic acid compound represented by the following formula (b3) or a carboxylic acid compound represented by the following formula (b4):

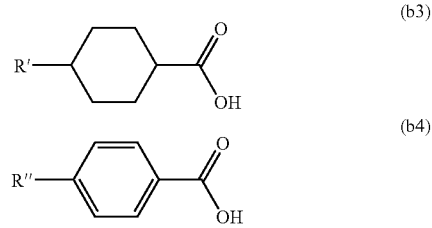

wherein R' and R" each independently represents linear alkyl or alkoxy having from 1 to 8 carbon atoms.

16. The cholesteric liquid crystal composition as claimed in claim 1, wherein the γ-oryzanol (A) contains the ferulate ester of a triterpene alcohol in an amount of 60% by weight or more.

17. The cholesteric liquid crystal composition as claimed in claim 1, wherein the cholesteric liquid crystal composition further contains at least one solvent selected from the group consisting of a fatty acid ester, a hydrocarbon, a higher alcohol, a lower alcohol, a polyhydric alcohol, a silicone oil, a cyclic ether, a ketone, an amide, an amino acid and an organic amine.

18. A microcapsule comprising a core material containing the cholesteric liquid crystal composition as claimed in claim 1, covered with a shell material.

19. The cholesteric liquid crystal composition as claimed in claim 1, wherein the cholesteric liquid crystal composition is applicable in one selected from the group consisting of a liquid crystal pigment, a paint, a spray ink, a printing ink, cosmetics, an anticounterfeit printed matter and an ornament.

20. Cosmetics comprising the cholesteric liquid crystal composition as claimed in claim 1.

21. The cosmetics as claimed in claim 20, wherein the cosmetics further contain at least one selected from the group consisting of a body pigment, a colorant, an antioxidant, an antioxidation assistant, an ultraviolet ray absorbent, a sequestering agent, a surfactant, a storage stabilizer, an antiseptic, a diluent, a plasticizer, a moisturizing agent, a viscosity controlling agent, a feel improver, a thickener, a film-forming agent, an ester oil, a liquid oil or fat, a solid oil or fat, wax, a water-soluble polymer, a cyclic ether, a ketone, an amide, an amino acid, an organic amine, a polyhydric alcohol, a polysaccharide, a polymer emulsion, a pH controlling agent, a vitamin, a skin nutrient, a perfume, an extract and water.

\* \* \* \* \*